United States Patent
Jang et al.

(10) Patent No.: US 10,727,516 B2
(45) Date of Patent: Jul. 28, 2020

(54) COMPOUND AND POLYMER ELECTROLYTE MEMBRANE USING SAME

(71) Applicant: LG CHEM, LTD., Seoul (KR)

(72) Inventors: Yong Jin Jang, Daejeon (KR); Joong Jin Han, Daejeon (KR); Sehee Jung, Daejeon (KR); Youngjea Kim, Daejeon (KR); Esder Kang, Daejeon (KR); Hyun Woog Ryu, Daejeon (KR)

(73) Assignee: LG CHEM, LTD., Seoul (KR)

( * ) Notice: Subject to any disclaimer, the term of this patent is extended or adjusted under 35 U.S.C. 154(b) by 103 days.

(21) Appl. No.: 15/519,978

(22) PCT Filed: Dec. 2, 2015

(86) PCT No.: PCT/KR2015/013091
§ 371 (c)(1),
(2) Date: Apr. 18, 2017

(87) PCT Pub. No.: WO2016/099050
PCT Pub. Date: Jun. 23, 2016

(65) Prior Publication Data
US 2017/0346121 A1 Nov. 30, 2017

(30) Foreign Application Priority Data

Dec. 19, 2014 (KR) .................. 10-2014-0184888
Nov. 30, 2015 (KR) .................. 10-2015-0168984

(51) Int. Cl.
| | |
|---|---|
| *H01M 8/1039* | (2016.01) |
| *H01M 8/18* | (2006.01) |
| *H01M 8/1025* | (2016.01) |
| *H01M 8/1027* | (2016.01) |
| *C07C 309/44* | (2006.01) |
| *H01M 8/1032* | (2016.01) |
| *C07C 317/14* | (2006.01) |

(52) U.S. Cl.
CPC ......... *H01M 8/1039* (2013.01); *C07C 309/44* (2013.01); *C07C 317/14* (2013.01); *H01M 8/1025* (2013.01); *H01M 8/1027* (2013.01); *H01M 8/1032* (2013.01); *H01M 8/184* (2013.01); *H01M 8/188* (2013.01); *H01M 2300/0082* (2013.01); *Y02E 60/528* (2013.01)

(58) Field of Classification Search
CPC .... H01M 8/184; H01M 8/188; H01M 8/1025; H01M 8/1027; H01M 8/1032; H01M 8/1039; H01M 2300/0082; C07C 309/44; C07C 317/14; Y02E 60/528
See application file for complete search history.

(56) References Cited

U.S. PATENT DOCUMENTS

| | | | |
|---|---|---|---|
| 3,022,320 A | 2/1962 | Bennett et al. | |
| 3,055,930 A | 9/1962 | Graf et al. | |
| 4,814,241 A * | 3/1989 | Nagashima | H01M 8/188 429/199 |
| 6,933,068 B2 * | 8/2005 | Asano | B01D 69/10 429/309 |
| 8,222,367 B2 | 7/2012 | Lalgudi et al. | |
| 2004/0044166 A1 * | 3/2004 | Rozhanskii | C07C 309/73 528/86 |
| 2005/0186460 A1 | 8/2005 | Kanaoka et al. | |
| 2009/0130525 A1 * | 5/2009 | Miyachi | B01D 67/0009 429/490 |
| 2009/0281270 A1 * | 11/2009 | Fuller | C08G 61/12 528/226 |
| 2010/0068592 A1 | 3/2010 | Akiyama et al. | |
| 2013/0034766 A1 | 2/2013 | Kim | |
| 2014/0377686 A1 | 12/2014 | Izuhara et al. | |
| 2015/0307659 A1 * | 10/2015 | Hong | C08G 65/4012 429/492 |

FOREIGN PATENT DOCUMENTS

| | | | |
|---|---|---|---|
| CN | 103998527 A | 8/2014 | |
| EP | 0 475 527 A2 | 3/1992 | |
| JP | 6-220025 A | 8/1994 | |
| JP | 2004-137444 A | 5/2004 | |
| JP | 2005-197236 A | 7/2005 | |
| JP | 2006-152009 A | 6/2006 | |
| JP | 2006-299080 A | 11/2006 | |
| JP | 2007-39554 A | 2/2007 | |
| JP | 2007-213937 A | 8/2007 | |
| JP | 2010-536151 A | 11/2010 | |
| JP | 2012-46741 A | 3/2012 | |
| JP | 2013-82931 A1 | 5/2013 | |
| KR | 10-2003-0076057 A | 9/2003 | |
| KR | 10-2013-0015228 A | 2/2013 | |
| WO | WO-2004050654 A1 * | 6/2004 | .......... C07D 207/14 |
| WO | WO 2014/034415 A1 | 3/2014 | |
| WO | WO-2014073934 A1 * | 5/2014 | ............ C08G 61/10 |

OTHER PUBLICATIONS

Derwent Abstract for WO 2004050654 A1. (Year: 2019).*
Abid et al., Synthesis and anti-cancer, anti-metastatic evaluation of some new fluorinated isocoumarins and 3,4-dihydroisocounnarins, Journal of Fluorine Chemistry (2012), 135, pp. 240-245. (Year: 2012).*
Jutemar et al., Copoly(arylene ether nitrile) and Copoly(arylene ether sulfone) Ionomers with Pendant Sulfobenzoyl Groups for Proton Conducting Fuel Cell Membranes, Journal of Polymer Science, Part A: Polymer Chemistry (2011), 49(3), pp. 734-745. (Year: 2011).*
Database Registry, 2009, RN 1097168-38-1, Retrieved from STNext [Online] (Retrieved on Aug. 7, 2019). (Year: 2009).*

(Continued)

*Primary Examiner* — Laura Weiner
(74) *Attorney, Agent, or Firm* — Birch, Stewart, Kolasch & Birch, LLP (57) ABSTRACT

The present specification relates to a novel compound, a polymer electrolyte membrane including the same, a membrane-electrode assembly including the polymer electrolyte membrane, a fuel cell including the membrane-electrode assembly, and a redox flow battery including the polymer electrolyte membrane.

14 Claims, 3 Drawing Sheets

(56) References Cited

OTHER PUBLICATIONS

Database CAPLUS, 2009, Abdellatif et al., "Poly(arylene ether)s carrying pendant (3-sulfonated) phenyl sulfonyl groups", Preprints of Symposia—American Chemical Society, Division of Fuel Chemistry (2009), 54(1), 190-191, Abstract Retrieved from STNext [Online] (Retrieved on Aug. 7, 2019). (Year: 2009).*
Abdellatif et al., "Poly(arylene ether)s carrying pendant (3-sulfonated) phenyl sulfonyl groups", Preprints of Symposia—American Chemical Society, Division of Fuel Chemistry (2009), 54(1), 190-191. (Year: 2009).*
Giam et al., "Evaluation of Ground-State Electronic Energy from Fluorine Nuclear Magnetic Resonance Shielding. I. Prediction of Enthalpies of Reaction for Formation of Lewis Acid Adducts of Benzophenones", Journal of the American Chemical Society, vol. 89, No. 10, May 10, 1967, pp. 2397-2401.
International Search Report issued in PCT/KR2015/013091 (PCT/ISA/210), dated Mar. 8, 2016.
Database Registry, 2009, RN 1154365-60-2, RN 1154365-44-2, Retrieved from STN international [online]; retrieved on Mar. 7, 2018.
Database Registry, 2010, RN 1242512-21-5, Retrieved from STN international [online]; retrieved on Mar. 6, 2018.
Jutemar et al., "Copoly(arylene ether nitrile) and Copoly(arylene ether sulfone) Ionomers with Pendant Sulfobenzoyl Groups for Proton Conducting Fuel Cell Membranes," Journal of Polymer Science, Part A: Polymer Chemistry, 2011, vol. 49, pp. 734-745.
Jutemar et al., "Facile Synthesis and Polymerization of 2,6-Difluoro-2'-sulfobenzophenone for Aromatic Proton Conducting Ionomers with Pendant Sulfobenzoyl Groups," Macromolecular Rapid Communications, 2010, vol. 31, pp. 1348-1353.
Jutemar et al., "Influence of the Polymer Backbone Structure on the Properties of Aromatic Ionomers with Pendant Sulfobenzoyl Side Chains for Use as Proton-Exchange Membranes," ACS Applied Materials & Interfaces, 2010, vol. 2, No. 12, pp. 3718-3725.
Li et al., "Fully Aromatic Ionomers with Precisely Sequenced Sulfona ed Moieties for Enhanced Proton Conductivity," Macromolecules, 2012, vol. 45, pp. 1447-1459.
European Search Report for Appl. No. 15870217.5 dated Apr. 16, 2018.
Parham, W.E., et al, "Synthesis of Isomeric Methyl Benzoylbenzoates and Substituted o-, m-, and p-Benzoylbenzoic acids," J. Org. Chem., Jul. 1, 1974, vol. 39, No. 14, pp. 2053-2056.

* cited by examiner

COMPOUND AND POLYMER ELECTROLYTE MEMBRANE USING SAME

TECHNICAL FIELD

This application claims priority to and the benefits of Korean Patent Application No. 10-2014-0184888, filed with the Korean Intellectual Property Office on Dec. 19, 2014, and Korean Patent Application No. 10-2015-0168984, filed with the Korean Intellectual Property Office on Nov. 30, 2015, the entire contents of which are incorporated herein by reference.

The present specification relates to a novel compound and a polymer electrolyte membrane using the same.

BACKGROUND ART

Korean Patent Application Laid-Open Publication No. 2003-0076057

DISCLOSURE

Technical Problem

The present specification is directed to providing a novel compound and a polymer electrolyte membrane using the same.

Technical Solution

One embodiment of the present specification provides a compound represented by the following Chemical Formula 1:

[Chemical Formula 1]

In Chemical Formula 1,

A is a sulfonyl group (—$SO_2$—) or a carbonyl group (—CO—),

R1, R3 and R5 are the same as or different from each other, and each independently hydrogen or a halogen group, R2 and R4 are the same as or different from each other, and each independently hydrogen, a hydroxyl group or a halogen group, R6 and R7 are the same as or different from each other, and each independently hydrogen or a halogen group, R8 to R10 are the same as or different from each other, and each independently selected from the group consisting of hydrogen, —$SO_3H$, —$SO_3^-M^+$, —COOH, —$COO^-M^+$, —$PO_3H_2$, —$PO_3H^-M^+$ and —$PO_3^{2-}2M^+$, at least one of R8 to R10 is selected from the group consisting of —$SO_3H$, —$SO_3^-M$, —COOH, —$COO^-M^+$, —$PO_3H_2$, —$PO_3H^-M^+$ and —$PO_3^{2-}2M^+$, M is a group 1 element, a is an integer of 0 to 3, and when a is an integer of 2 or greater, a plurality of R6s and R7s are each independently the same as or different from each other.

One embodiment of the present specification provides a polymer including a monomer derived from the compound of Chemical Formula 1.

One embodiment of the present specification provides a polymer electrolyte membrane including a polymer including a monomer derived from the compound of Chemical Formula 1.

In addition, one embodiment of the present specification provides a membrane-electrode assembly including an anode; a cathode; and the polymer electrolyte membrane described above provided between the anode and the cathode.

In addition, one embodiment of the present specification provides a polymer electrolyte-type fuel cell including two or more of the membrane-electrode assemblies described above; a stack including a bipolar plate provided between the membrane-electrode assemblies; a fuel supplying unit supplying fuel to the stack; and an oxidizer supplying unit supplying an oxidizer to the stack.

One embodiment of the present specification also provides a redox flow battery including a positive electrode cell including a positive electrode and a positive electrode liquid electrolyte; a negative electrode cell including a negative electrode and a negative electrode liquid electrolyte; and the polymer electrolyte membrane described above provided between the positive electrode cell and the negative electrode cell.

Advantageous Effects

A monomer derived from a compound according to one embodiment of the present specification provides high reactivity in a polymerization reaction process.

In addition, a polymer electrolyte membrane including a compound according to one embodiment of the present specification has excellent durability.

Furthermore, a fuel cell and/or a redox flow battery including the polymer electrolyte membrane have excellent durability and efficiency.

REFERENCE NUMERAL

100: Electrolyte Membrane
200a: Anode
200b: Cathode
10, 20: Tank
11, 21: Pump
31: Electrolyte Membrane
32: Positive Electrode Cell
33: Negative Electrode Cell
41: Positive Electrode Liquid Electrolyte
42: Negative Electrode Liquid Electrolyte
60: Stack
70: Oxidizer Supplying Unit
80: Fuel Supplying Unit
81: Fuel Tank
82: Pump

MODE FOR DISCLOSURE

Hereinafter, the present specification will be described in more detail.

According to one embodiment of the present specification, M, a group 1 element, may be Li, Na or K.

According to one embodiment of the present specification, at least one of R1 to R7 is a halogen group, and the halogen group is selected from between chlorine and fluorine.

According to one embodiment of the present specification, at least one of R1 to R5 is a halogen group.

According to one embodiment of the present specification, at least one of R1 to R5 is a halogen group, and the halogen group is selected from between chlorine and fluorine.

According to one embodiment of the present specification, at least two of R1 to R5 are a halogen group.

According to one embodiment of the present specification, at least two of R1 to R5 are a halogen group, and the halogen group is selected from between chlorine and fluorine.

Specifically, when two of R1 to R5 are a halogen group, the two halogen groups may be in a meta relation. This is effective in more efficiently progressing a reaction in the polymerization reaction.

According to one embodiment of the present specification, at least three of R1 to R5 are a halogen group.

In the compound represented by Chemical Formula 1, functional groups capable of a nucleophilic reaction such as a halogen group and a hydroxyl group are present in the benzene ring substituted with R1 to R5, however, functional groups capable of a nucleophilic reaction such as a halogen group and a hydroxyl group are not present in the benzene ring substituted with R8 to R10. Accordingly, in the polymerization reaction represented by Chemical Formula 1, a target polymer having the benzene ring substituted with R1 to R5 as a main chain, and the benzene ring substituted with R8 to R10 linked in a pendant form thereto may be obtained instead of a form having side branches spreading in several directions.

According to one embodiment of the present specification, R1 and R3 are a halogen group, and R2, R4 and R5 are hydrogen. Due to an electron withdrawing effect of a sulfonyl group (—SO$_2$—) or a carbonyl group (—CO—) corresponding to A of Chemical Formula 1, reactivity at the ortho or para position with respect to the carbon substituted with A relatively increases, which resultantly leads to an advantage of enhancing reactivity in the polymerization reaction. Accordingly, when R1 and R3 are a halogen group, and R2, R4 and R5 are hydrogen according to one embodiment of the present specification, there is an advantage in that high reactivity is exhibited in the polymerization reaction.

Specifically, according to one embodiment of the present specification, the above-mentioned advantage may be maximized when R1 and R3 are fluorine, and R2, R4 and R5 are hydrogen.

In the present specification, the case of R1 and R3 being a halogen group and R2, R4 and R5 being hydrogen is the same as the case of R3 and R5 being a halogen group and R1, R2 and R4 being hydrogen. This is due to the fact that the single bond linked to linker A is rotatable.

According to one embodiment of the present specification, R1 and R5 are a halogen group, and R2 to R4 are hydrogen.

In the compound represented by Chemical Formula 1 according to one embodiment of the present specification, R8 to R10 are at the ortho and/or para position with respect to the carbon substituted with a linker connecting the two benzene rings. The linker connecting the two benzene rings includes a sulfonyl group (—SO$_2$—) or a carbonyl group (—CO—) exhibiting an electron withdrawing effect, and due to these groups, acidity of the ion transfer functional groups (R8 to R10) at the ortho and/or para position increases. As a result, a polymer electrolyte membrane including a polymer including the same has an advantage of exhibiting enhanced cation conductivity. This advantage may be maximized when the sulfonyl group (—SO$_2$—) or the carbonyl group (—CO—) directly links the two benzene rings. Specifically, according to one embodiment of the present specification, a is 0.

According to one embodiment of the present specification, A is a carbonyl group.

According to one embodiment of the present specification, A is a carbonyl group, and a is 0.

In the present specification, a being 0 means a direct bond.

According to one embodiment of the present specification, A is a carbonyl group, R1 and R3 are a halogen group, R2, R4 and R5 are hydrogen, and a is 0.

According to one embodiment of the present specification, A is a carbonyl group, R1 and R3 are fluorine, R2, R4 and R5 are hydrogen, and a is 0.

According to one embodiment of the present specification, A is a carbonyl group, R1 and R3 are a halogen group, R2, R4 and R5 to R7 are hydrogen, and a is 0.

According to one embodiment of the present specification, A is a carbonyl group, R1 and R3 are fluorine, R2, R4 and R5 to R7 are hydrogen, and a is 0.

According to one embodiment of the present specification, A is a sulfonyl group. An electrolyte membrane including a copolymer introducing a sulfonyl group instead of a carbonyl group has an advantage of enhancing durability. This is caused by chemical stability of a sulfonyl group that is not readily decomposed by strong acids of the electrolyte or radicals generated in the electrolyte.

According to one embodiment of the present specification, A is a sulfonyl group, and a is an integer of 1 to 3. By adding alkylene between the sulfonyl group and the benzene rings substituted with an ion transfer functional group, flexibility may be provided.

According to one embodiment of the present specification, R6 and R7 are hydrogen.

According to one embodiment of the present specification, at least one of R6 and R7 is a halogen group.

According to one embodiment of the present specification, at least one of R6 and R7 is fluorine.

According to one embodiment of the present specification, R6 and R7 are a halogen group.

According to one embodiment of the present specification, R6 and R7 are fluorine.

In the present specification, at least one of R8 to R10 is an ion transfer functional group, and the ion transfer functional group is located at the ortho and/or para position with respect to the linker (-A-[CR6R7]a-) connecting the two benzene rings. As described above, by the ion transfer functional group locating at the ortho and/or para position, enhanced reactivity may be exhibited in the polymerization reaction.

According to one embodiment of the present specification, at least one of R8 to R10 is —SO$_3$H or —SO$_3^-$M$^+$. The sulfonic acid group absorbs a maximum of approximately 10 moles of water per 1 mole, and exhibits high proton conductivity of approximately 0.1 Scm$_{-1}$.

According to one embodiment of the present specification, the compound represented by Chemical Formula 1 may be any one selected from among the following structures.

1-a

1-b

1-c

1-d

1-e

1-f

1-g 1-h

1-i

1-j 1-k 1-l

1-m 1-n 1-o 1-p 1-q

The compound represented by Chemical Formula 1 may be prepared based on preparation examples to be described below. Based on the preparation examples to be described below, those skilled in the art may prepare compounds of Chemical Formula 1 other than those prepared in the preparation examples.

One embodiment of the present specification also provides a polymer including a monomer derived from the compound represented by Chemical Formula 1. As described above, the monomer has an advantage of exhibiting enhanced reactivity in the polymerization reaction.

The polymer according to one embodiment of the present specification has the benzene ring substituted with R1 to R5 as a main chain, and the benzene ring substituted with R8 to R10 linked thereto in a pendant form.

In the present specification, a "monomer" means a structure in which a compound is included in a divalent or higher form in a polymer through a polymerization reaction. Specifically, a monomer derived from the compound represented by Chemical Formula 1 may have a structure as follows. However, the structure is not limited thereto.

Polymers included in existing polymer electrolyte membranes generally have a structure in which an ion transfer functional group such as a sulfonic acid group is located on the main chain. However, the polymer according to one embodiment of the present specification has a structure in which the benzene ring substituted with an ion transfer functional group such as a sulfonic acid group is located in a pendant form rather than being the main chain. Accordingly, in a polymer electrolyte membrane including the polymer, ion channels are readily formed, which resultantly leads to an advantage of obtaining an effect of enhancing ion conductivity.

According to one embodiment of the present specification, the monomer derived from the compound represented by Chemical Formula 1 may be included in 0.1 mol % to 100 mol % of monomers forming the whole polymer. Specifically, the polymer includes only the monomer derived from the compound represented by Chemical Formula 1. In another embodiment, the polymer may include a second monomer in addition to the monomer derived from the compound represented by Chemical Formula 1. In this case, content of the monomer derived from the compound represented by Chemical Formula 1 is preferably from 0.5 mol % to 60 mol %. More preferably, the content may be from 5 mol % to 60 mol %. A polymer including the monomer derived from the compound in the above-mentioned range has mechanical strength and high ion conductivity.

As the second monomer, those known in the art may be used. Herein, the second monomer may be used in one, two or more types.

Examples of the second monomer may include monomers forming perfluorosulfonic acid polymers, hydrocarbon-based polymers, polyimide, polyvinylidene fluoride, polyether sulfone, polyphenylene sulfide, polyphenylene oxide, polyphosphazene, polyethylene naphthalate, polyester, doped polybenzimidazole, polyetherketone, polysulfone, acids thereof, or bases thereof.

According to one embodiment of the present specification, content of the second monomer in the polymer may be greater than 0% by weight and less than or equal to 95% by weight.

According to one embodiment of the present specification, when the polymer includes the second monomer, the polymer may be a random polymer.

One embodiment of the present specification also provides a polymer electrolyte membrane including the polymer. The polymer electrolyte membrane may exhibit effects described above. The monomer derived from Chemical Formula 1 performs a role of controlling ion conductivity of the polymer electrolyte membrane.

In the present specification, the "electrolyte membrane" includes, as a membrane capable of exchanging ions, a membrane, an ion-exchange membrane, an ion-transfer membrane, an ion-conductive membrane, a separator, an ion-exchange separator, an ion-transfer separator, an ion-conductive separator, an ion-exchange electrolyte membrane, an ion-transfer electrolyte membrane, an ion-conductive electrolyte membrane or the like.

The polymer electrolyte membrane according to the present specification may be prepared using materials and/or methods known in the art except that the polymer electrolyte membrane includes the monomer derived from the compound represented by Chemical Formula 1.

According to another embodiment, a weight average molecular weight of the polymer included in the polymer electrolyte membrane may be greater than or equal to 10,000 and less than or equal to 5,000,000 (g/mol), specifically, greater than or equal to 20,000 and less than or equal to 2,000,000 (g/mol), and more specifically, greater than or equal to 50,000 and less than or equal to 1,000,000 (g/mol).

According to one embodiment of the present specification, the polymer electrolyte membrane has an ion exchange capacity (IEC) value of 0.01 mmol/g to 5 mmol/g. When the polymer electrolyte membrane has an ion exchange capacity value in the above-mentioned range, ion channels are formed in the polymer electrolyte membrane, and the polymer may exhibit ion conductivity.

When the copolymer has a weight average molecular weight of greater than or equal to 500 and less than or equal to 5,000,000 (g/mol), mechanical properties of the electrolyte membrane do not decline, and proper polymer solubility is maintained, and as a result, the electrolyte membrane may be readily manufactured.

According to one embodiment of the present specification, the electrolyte membrane may have a thickness of 1 μm to 500 μm, and specifically 10 μm to 200 μm. When the electrolyte membrane has a thickness of 1 μm to 500 μm, electric short and electrolyte material cross over are reduced, and an excellent cation conductivity property may be exhibited.

According to one embodiment of the present specification, the polymer electrolyte membrane has ion conductivity of greater than or equal to 0.01 S/cm and less than or equal to 0.5 S/cm. In another embodiment, the polymer electrolyte membrane may have ion conductivity of greater than or equal to 0.01 S/cm and less than or equal to 0.3 S/cm. The ion conductivity may mean values measured under a condition of room temperature and RH=100%.

According to one embodiment of the present specification, at least a part of the polymer may have a metal salt form. In addition, the metal salt may be substituted with an acid form.

Specifically, an electrolyte membrane including a polymer substituted with hydrogen (H) instead of metal M may be formed by adding an acid solution to polymers having at least one of R8 to R10 being —$SO_3^-M^+$, —$COO^-M^+$, —$PO_3H^-M^+$ or —$PO_3^{2-}2M^+$ in Chemical Formula 1.

According to one embodiment of the present specification, general acid solutions may be used in the acid treatment, and specifically, hydrochloric acid or sulfuric acid may be used.

According to one embodiment of the present specification, the acid solution may have a concentration of greater than or equal to 0.1 M and less than or equal to 10 M, and specifically, greater than or equal to 1 M and less than or equal to 2 M. When the acid solution has a concentration of greater than or equal to 0.1 M and less than or equal to 10 M, substitution with hydrogen instead of metal M may be readily carried out without damaging the electrolyte membrane.

One embodiment of the present specification also provides a membrane-electrode assembly including an anode; a cathode; and the polymer electrolyte membrane described above provided between the anode and the cathode.

The membrane-electrode assembly (MEA) means an assembly of electrodes (cathode and anode) in which an electrochemical catalyst reaction of fuel and air occurs and a polymer membrane in which hydrogen ion transfer occurs, and is a single assembled unit in which electrodes (cathode and anode) and an electrolyte membrane are adhered.

The membrane-electrode assembly of the present specification has a form of a catalyst layer of an anode and a catalyst layer of a cathode being brought into contact with an electrolyte membrane, and may be prepared using common methods known in the art. As one example, the membrane-electrode assembly may be prepared through thermocompressing the cathode; the anode; and the electrolyte membrane located between the cathode and the anode at 100° C. to 400° C. while sticking these together.

The anode electrode may include an anode catalyst layer and an anode gas diffusion layer. The anode gas diffusion layer may again include an anode micropore layer and an anode electrode substrate.

The cathode electrode may include a cathode catalyst layer and a cathode gas diffusion layer. The cathode gas diffusion layer may again include a cathode micropore layer and a cathode electrode substrate.

Figure 1:
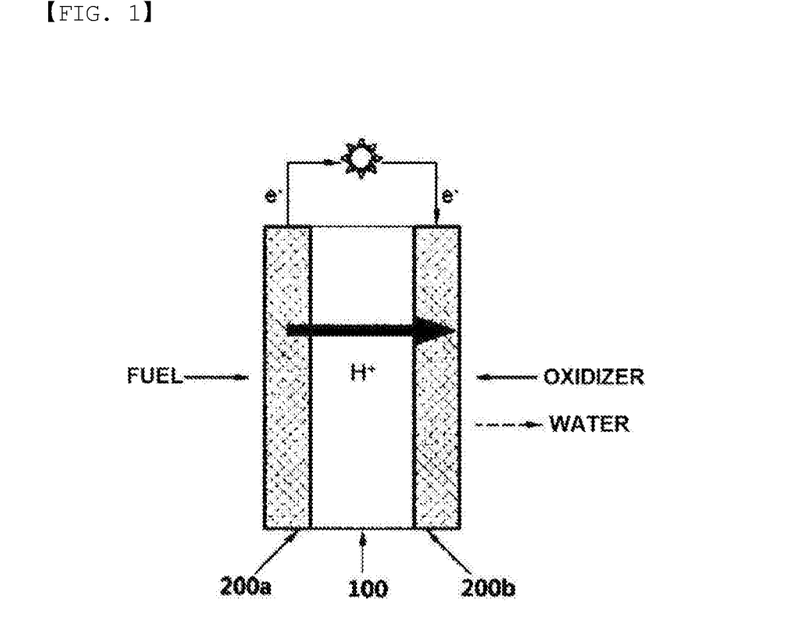
FIG. 1 is a schematic diagram showing a principle of electricity generation of a fuel cell.

FIG. 1 is a schematic diagram showing a principle of electricity generation of a fuel cell, and in the fuel cell, a most basic unit generating electricity is a membrane-electrode assembly (MEA), and this is formed with an electrolyte membrane (100), and anode (200*a*) and cathode (200*b*) electrodes formed on both sides of the electrolyte membrane (100). When referring to FIG. 1 showing a principle of electricity generation of a fuel cell, an oxidation reaction of fuel such as hydrogen or hydrocarbon such as methanol and butane occurs in the anode (200*a*) to generate hydrogen ions (H$^+$) and electrons (e$^-$), and the hydrogen ions migrate to the cathode (200*b*) through the electrolyte membrane (100). In the cathode (200*b*), water is produced through the reaction of the hydrogen ions transferred through the electrolyte membrane (100), an oxidizer such oxygen, and electrons. Electrons migrate to an external circuit through such a reaction.

The anode electrode catalyst layer is a place where an oxidation reaction of fuel occurs, and catalysts selected from the group consisting of platinum, ruthenium, osmium, platinum-ruthenium alloys, platinum-osmium alloys, platinum-palladium alloys and platinum-transition metal alloys may be preferably used. The cathode electrode catalyst layer is a place where a reduction reaction of an oxidizer occurs, and platinum or platinum-transition metal alloys may be preferably used as catalysts. The catalysts may be used as they are, or may be used while being supported on a carbon-based carrier.

The process of introducing the catalyst layer may be carried out using common methods known in the art, and for example, a catalyst ink may be directed coated on the electrolyte membrane, or a catalyst ink may be coated on the gas diffusion layer to form the catalyst layer. Herein, the coating method of the catalyst ink is not particularly limited, and methods of spray coating, tape casting, screen printing, blade coating, die coating, spin coating or the like may be used. The catalyst ink may be typically formed with a catalyst, a polymer ionomer and a solvent.

The gas diffusion layer becomes a migration path of reaction gases and water while performing a role of a current conductor, and has a porous structure. Accordingly, the gas diffusion layer may be formed including a conductive substrate. As the conductive substrate, carbon paper, carbon cloth or carbon felt may be preferably used. The gas diffusion layer may be formed further including a micropore layer between the catalyst layer and the conductive substrate. The micropore layer may be used for enhancing fuel cell performance under a low humidity condition, and performs a role of allowing the electrolyte membrane to be under a sufficiently wet condition by having the amount of water escaping outside the gas diffusion layer being small.

One embodiment of the present specification provides a polymer electrolyte-type fuel cell including two or more of the membrane-electrode assemblies; a stack including a bipolar plate provided between the membrane-electrode assemblies; a fuel supplying unit supplying fuel to the stack; and an oxidizer supplying unit supplying an oxidizer to the stack.

When using the electrolyte membrane according to one embodiment of the present specification as an ion-exchange membrane of a fuel cell, effects described above may be obtained.

A fuel cell is an energy conversion device directly converting chemical energy of fuel into electric energy. In other words, a fuel cell employs a power generation method utilizing a fuel gas and an oxidizer, and using electrons generated during the oxidation and reduction reactions of these to produce power.

The fuel cell may be prepared through common methods known in the art using the membrane-electrode assembly (MEA) described above. For example, the fuel cell may be prepared forming with the membrane-electrode assembly (MEA) prepared above and a bipolar plate.

The fuel cell of the present specification is formed including a stack, a fuel supplying unit and an oxidizer supplying unit.

Figure 3:
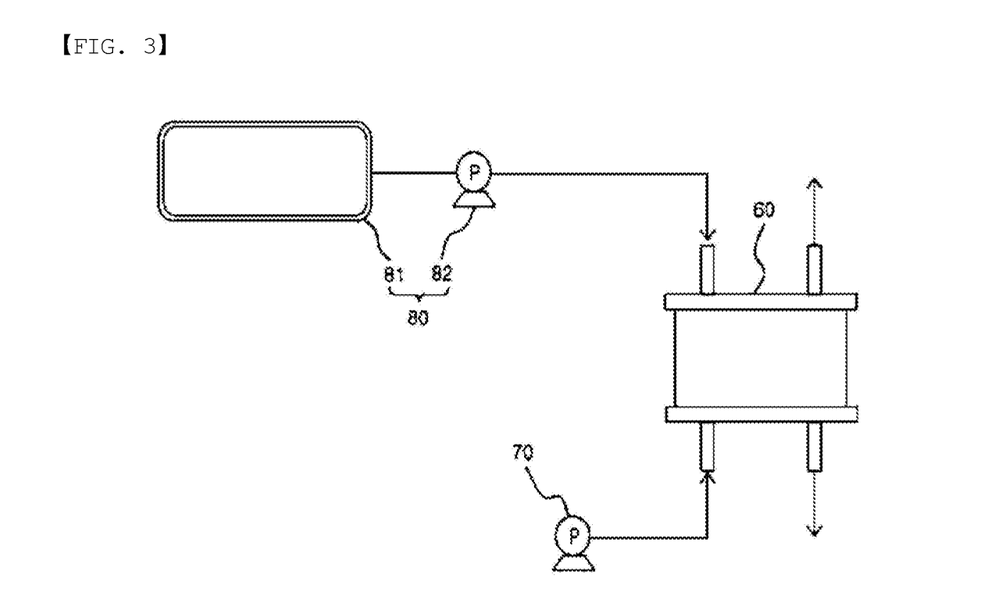
FIG. 3 is a diagram schematically illustrating one embodiment of a fuel cell.

FIG. 3 is a diagram schematically illustrating the fuel cell, and the fuel cell is formed including a stack (60), an oxidizer supplying unit (70) and a fuel supplying unit (80).

The stack (60) includes one, two or more of the membrane-electrode assemblies described above, and when two or more of the membrane-electrode assemblies are included, a separator provided therebetween is included. The separator prevents the membrane-electrode assemblies from being electrically connected, and performs a role of transferring fuel and oxidizer supplied from the outside to the membrane-electrode assemblies.

The oxidizer supplying unit (70) performs a role of supplying an oxidizer to the stack (60). As the oxidizer, oxygen is typically used, and oxygen or air may be injected with a pump (70) to be used.

The fuel supplying unit (80) performs a role supplying fuel to the stack (60), and may be formed with a fuel tank (81) storing fuel, and a pump (82) supplying the fuel stored in the fuel tank (81) to the stack (60). As the fuel, hydrogen or hydrocarbon fuel in a gas or liquid state may be used. Examples of the hydrocarbon fuel may include methanol, ethanol, propanol, butanol or natural gas.

The fuel cell may include a polymer electrolyte fuel cell, a direct liquid fuel cell, a direct methanol fuel cell, a direct formic acid fuel cell, a direct ethanol fuel cell, a direct dimethyl ether fuel cell or the like.

In addition, one embodiment of the present specification provides a redox flow battery including a positive electrode cell including a positive electrode and a positive electrode liquid electrolyte; a negative electrode cell including a negative electrode and a negative electrode liquid electrolyte; and the polymer electrolyte membrane according to one embodiment of the present specification provided between the positive electrode cell and the negative electrode cell.

A redox flow battery (oxidation-reduction flow battery) is a system charged and discharged by active materials included in a liquid electrolyte being oxidized and reduced, and is an electrochemical storage device directly storing chemical energy of the active materials as electric energy. A redox flow battery uses a principle of being charged and discharged from the exchange of electrons occurring when liquid electrolytes including active materials in different oxidation states meet with an ion-exchange membrane in between. A redox flow battery is generally formed with a tank holding a liquid electrolyte, a battery cell where charge and discharge occur, and a circulating pump for circulating the liquid electrolyte between the tank and the battery cell, and a unit cell of the battery cell includes an electrode, an electrolyte and an ion-exchange membrane.

When using the electrolyte membrane according to one embodiment of the present specification as an ion-exchange membrane of the redox flow battery, effects described above may be obtained.

The redox flow battery of the present specification may be prepared using common methods known in the art except that the redox flow battery includes the polymer electrolyte membrane according to one embodiment of the present specification.

Figure 2:
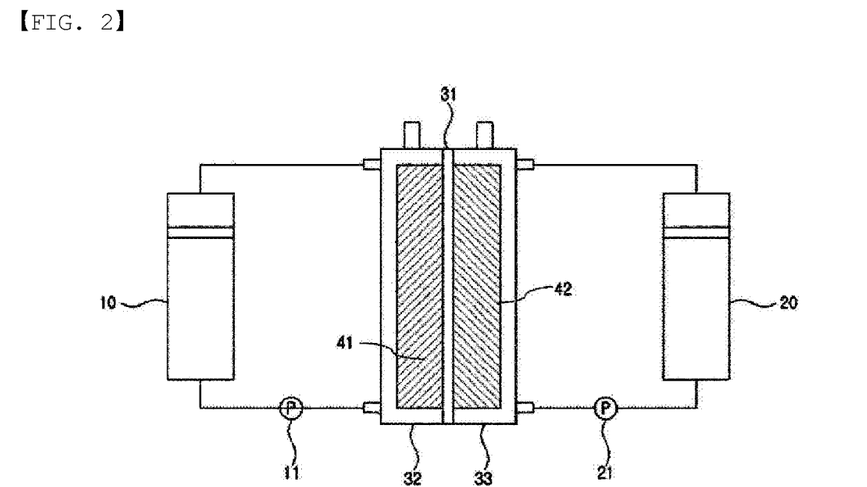
FIG. 2 is a diagram schematically illustrating a general structure of a redox flow battery.

As illustrated in FIG. 2, the redox flow battery is divided into a positive electrode cell (32) and a negative electrode cell (33) by an electrolyte membrane (31). The positive electrode cell (32) and the negative electrode cell (33) include a positive electrode and a negative electrode, respectively. The positive electrode cell (32) is connected to a positive electrode tank (10) for supplying and releasing a positive electrode liquid electrolyte (41) through a pipe. The negative electrode cell (33) is also connected to a negative electrode tank (20) for supplying and releasing a negative electrode liquid electrolyte (42) through a pipe. The liquid electrolytes circulate through pumps (11, 21), and through an oxidation/reduction reaction (that is, a redox reaction)

changing the oxidation number of ions, charge and discharge occur in the positive electrode and the negative electrode.

One embodiment of the present specification also provides a method for preparing the polymer electrolyte membrane. The polymer electrolyte membrane may be prepared using materials and/or methods in the art except that a polymer including a monomer derived from the compound represented by Chemical Formula 1 is included. For example, the polymer electrolyte membrane may be prepared by preparing a polymer solution through adding the polymer to a solvent, and then forming a film using a solution casting method.

Hereinafter, the present specification will be described in more detail with reference to examples. However, the following examples are for illustrative purposes only, and the scope of the present specification is not limited thereto.

Compound Preparation Example 1

A compound represented by Chemical Formula 1 when A of Chemical Formula 1 is a carbonyl group (—CO—) and a is 0 may be prepared in a manner as in the following Reaction Formula 1.

[Reaction Formula 1]

After dissolving 176 mg (0.92 mmol) of 1-bromo-2,4-difluorobenzene in 3 ml of anhydrous diethyl ether, the result was cooled to −78° C. under nitrogen gas. 0.57 ml (0.92 mmol) of n-BuLi (1.6 M hexane solvent) was slowly added dropwise to the reactant, and then the result was stirred for 30 minutes at the same temperature. 168 mg (0.92 mmol) of 3H-benzo[c][1,2]oxathiol-3-one-1,1-dioxide was dissolved in 2 ml of anhydrous diethyl ether and slowly added to the reactant, and then the reaction temperature was slowly raised to room temperature. The reaction was terminated using a saturated aqueous ammonium chloride solution, the result was acidified with 1 N HCl, and the compound was extracted with ethyl acetate. The reactant was separated and purified by prep-TLC chromatography $CH_2Cl_2$:MeOH=9:1 to obtain 171.4 mg (yield 63%) of a final compound.

1H NMR (500 MHz, DMSO-D6) δ 8.5 (1H, brs), 8.09 (1H, m), 7.90 (3H, m), 7.70 (1H, m), 7.16 (1H, m), 6.78 (2H, m)

$[M+H]^+=298$

Compound Preparation Example 2

A compound represented by Chemical Formula 1 when A of Chemical Formula 1 is a sulfonyl group (—$SO_2$—) and a is 0 may be prepared in a manner as in the following Reaction Formula 2.

[Reaction Formula 2]

After dissolving 101 mg (0.69 mmol) of 2,4-difluorobenzenethiol in 4 ml of n-BuOH, 163.8 mg (0.69 mmol) of 4-bromobenzenesulfonic acid, 298.9 mg (3.1 mmol) of NaOtBu and 4 mg (0.035 mmol) of $Pd(PPh_3)_4$ were consecutively added dropwise thereto. The reactant was heated to raise the temperature to 110° C., the result was stirred for 3 hours at the same temperature and cooled to room temperature, and the filtrate obtained from filtration using a celite pad was vacuum distilled.

The compound was dissolved in water and then acidified using 1 N HCl, and extracted with ethyl acetate. This organic layer was washed with a saturated aqueous sodium chloride solution, dried with $MgSO_4$ and vacuum distilled, and an obtained crude compound was separated and purified by prep-TLC chromatography $CH_2Cl_2$:MeOH=9:1 to obtain 137.9 mg (yield 66%) of 4-((2,4-difluorophenyl)thio)benzenesulfonic acid.

After dissolving 137.9 mg (0.46 mmol) of 4-((2,4-difluorophenyl)thio)benzenesulfonic acid obtained above in 10 ml of acetonitrile solvent, 5 ml of hydrogen peroxide solution was slowly added dropwise thereto at 0° C. After the reactant was reacted for 12 hours at room temperature, acetonitrile, the solvent, was removed by vacuum distillation, and the water layer was acidified with 1 N HCl and then extracted with ethyl acetate. The organic layer was dried with MgSO₄ and vacuum distilled to obtain 129.7 mg (yield 85%) of a final compound.

¹H NMR (500 MHz, DMSO-D6) δ 8.52 (1H, brs), 8.11 (2H, d), 7.97 (2H, d), 7.72 (1H, m), 7.09 (1H, m), 6.85 (1H, m)

[M+H]⁺=334

Compound Preparation Example 3

A compound represented by Chemical Formula 1 when A of Chemical Formula 1 is a sulfonyl group (—SO₂—) and a is 0 may be prepared in a manner as in the following Reaction Formula 3.

[Reaction Formula 3]

After dissolving 1.24 g (8.45 mmol) of 2,4-difluorobenzenethiol in 20 ml of DMF solvent, 2.12 g (8.45 mmol) of 4-(bromomethyl)benzenesulfonic acid and 3.5 g (25.35 mmol) of K₂CO₃ were consecutively added dropwise thereto. After the result was stirred for 12 hours at room temperature, the reaction was terminated using a saturated aqueous ammonium chloride solution, the result was acidified with 1 N HCl, and the DMF solvent was removed by vacuum distillation under high pressure. The reactant was dissolved in ethyl acetate, washed with a saturated aqueous sodium chloride solution, dried with MgSO₄, and then vacuum distilled.

The obtained solid compound was made to a slurry state in a methylene chloride solvent and then filtered, and dried under nitrogen gas to obtain 819 mg (yield 30.7%) of 4-(((2,4-difluorophenyl)thio)methyl)benzene sulfonic acid.

After dissolving 819 mg (2.59 mmol) of 4-(((2,4-difluorophenyl)thio)methyl)benzene sulfonic acid obtained above in 10 ml of acetonitrile solvent, 5 ml of hydrogen peroxide solution was slowly added dropwise thereto at 0° C. After the reactant was reacted for 12 hours at room temperature, acetonitrile, the solvent, was removed by vacuum distillation, and the water layer was acidified with 1 N HCl, and then extracted with ethyl acetate. The organic layer was dried with MgSO₄ and vacuum distilled to obtain 802.6 mg (yield 89%) of a final compound.

¹H NMR (500 MHz, DMSO-D6) δ 8.45 (1H, brs), 7.75 (3H, m), 7.51 (2H, m), 7.27 (1H, m), 7.03 (1H, m), 5.17 (1H, s)

[M+H]⁺=348

Preparation examples of the compound represented by Chemical Formula 1 is not limited to Reaction Formulae 1 to 3, and the compound of Chemical Formula 1 may be prepared using starting materials and reaction conditions known in the art.

<Polymer Synthesis Example 1> Synthesis of Random Polymer

Each monomer and potassium carbonate ($K_2CO_3$: molar ratio 4) were mixed in a 20 wt % ratio of NMP and a 20 wt % ratio of benzene, and the result was polymerized for 4 hours at 140° C. and 16 hours at 180° C. to prepare the polymer.

Example 1

A separator was prepared using the polymer obtained in Polymer Synthesis Example 1, and a molecular weight thereof was measured through GPC, and results of measuring cation conductivity and ion exchange capacity (IEC) of the pure membrane were described.

TABLE 1

| | Mn (g/mol) | Mw (g/mol) | Mw/Mn | Ion Conductivity (S/cm) | Ion Exchange Capacity |
|---|---|---|---|---|---|
| Example 1 | 82,000 | 612,000 | 7.46 | 0.134 | 1.31 |

Comparative Example 1

A polymer was prepared in the same manner as in Example 1 using a monomer having sulfonic acid at a meta position based on the sulfonyl linker. A separator was prepared using the polymer, and results of measuring cation conductivity and ion exchange capacity (IEC) of the pure membrane are shown in the following Table 2.

TABLE 2

| Partial Fluorine-based Membrane | Ion Conductivity (S/cm) | Ion Exchange Capacity |
|---|---|---|
| Example 1 | 0.134 | 1.31 |
| Comparative Example 1 | 0.098 | 1.30 |

From the results of Table 2, it was seen that cation conductivity of the pure membrane using the polymer having sulfonic acid in the benzene ring at a para position rather than a meta position based on the sulfonyl linker is far higher under the same condition, and performance of the separator was enhanced.

The invention claimed is:

1. A compound represented by the following Chemical Formula 1:

wherein, in Chemical Formula 1,
A is a sulfonyl group (—$SO_2$—);
R1 and R3 are each independently selected from the group consisting of fluorine and chlorine, and R2, R4 and R5 are hydrogen;
at least one of R1 and R3 is fluorine;
R6 and R7 are the same as or different from each other, and each are independently hydrogen or a halogen group;
R8 to R10 are the same as or different from each other, and each are independently selected from the group consisting of hydrogen, —$SO_3H$, —$SO_3^-M^+$, —COOH, —$COO^-M^+$, —$PO_3H_2$, —$PO_3H^-M^+$ and —$PO_3^{2-}2M^+$;
at least one of R8 to R10 is selected from the group consisting of —$SO_3H$, —$SO_3^-M^+$, —COOH, —$COO^-M^+$, —$PO_3H_2$, —$PO_3H^-M^+$ and —$PO_3^{2-}2M^+$,
M is Li, Na or K;
a is an integer of 0 to 3; and
when a is an integer of 2 or 3, a plurality of R6s and R7s are each independently the same as or different from each other.

2. The compound of claim 1, wherein at least one of R8 to R10 is —$SO_3H$ or —$SO_3^-M^+$.

3. The compound of claim 1, wherein a is 0.

4. The compound of claim 1, wherein a is an integer of 1 to 3.

5. The compound of claim 1, wherein the compound represented by Chemical Formula 1 is any one selected from among the following structures:

1-c

1-d 1-e 1-f 1-h 1-i

-continued 1-j 1-k 1-p 1-t

6. A polymer comprising a monomer derived from the compound of claim 1.

7. The polymer of claim 6, which includes the monomer in 0.1 mol % to 100 mol %.

8. A polymer electrolyte membrane comprising the polymer of claim 6.

9. The polymer electrolyte membrane of claim 8, wherein the polymer has a weight average molecular weight of greater than or equal to 500 g/mol and less than or equal to 5,000,000 g/mol.

10. The polymer electrolyte membrane of claim 8, which has a thickness of greater than or equal to 1 μm and less than or equal to 500 μm.

11. The polymer electrolyte membrane of claim 8, which has ion conductivity of greater than or equal to 0.01 S/cm and less than or equal to 0.5 S/cm.

12. A membrane-electrode assembly comprising:
an anode;
a cathode; and
the polymer electrolyte membrane of claim 8 provided between the anode and the cathode.

13. A polymer electrolyte-type fuel cell comprising:
two or more of the membrane-electrode assemblies of claim 12;
a stack including a bipolar plate provided between the membrane-electrode assemblies;
a fuel supplying unit supplying fuel to the stack; and
an oxidizer supplying unit supplying an oxidizer to the stack.

14. A redox flow battery comprising:
a positive electrode cell including a positive electrode and a positive electrode liquid electrolyte;
a negative electrode cell including a negative electrode and a negative electrode liquid electrolyte; and
the polymer electrolyte membrane of claim 8 provided between the positive electrode cell and the negative electrode cell.

* * * * *